United States Patent
Majeed et al.

(10) Patent No.: US 9,635,862 B2
(45) Date of Patent: *May 2, 2017

(54) **METHOD OF PRODUCING PARTIALLY PURIFIED EXTRACELLULAR METABOLITE PRODUCTS FROM *BACILLUS COAGULANS* AND BIOLOGICAL APPLICATIONS THEREOF**

(71) Applicants: Muhammed Majeed, Edison, NJ (US); Kalyanam Nagabhushanam, East Windsor, NJ (US); Sivakumar Arumugam, Bangalore (IN); Furqan Ali, Bangalore (IN)

(72) Inventors: Muhammed Majeed, Edison, NJ (US); Kalyanam Nagabhushanam, East Windsor, NJ (US); Sivakumar Arumugam, Bangalore (IN); Furqan Ali, Bangalore (IN)

(73) Assignee: SAMI LABS LIMITED, Bangalore (IN)

( * ) Notice: Subject to any disclaimer, the term of this patent is extended or adjusted under 35 U.S.C. 154(b) by 0 days.

This patent is subject to a terminal disclaimer.

(21) Appl. No.: 15/214,699

(22) Filed: Jul. 20, 2016

(65) Prior Publication Data

US 2016/0324163 A1 Nov. 10, 2016

Related U.S. Application Data

(62) Division of application No. 14/576,411, filed on Dec. 19, 2014.

(60) Provisional application No. 61/920,567, filed on Dec. 24, 2013.

(51) Int. Cl.

| | |
|---|---|
| *A61K 35/00* | (2006.01) |
| *A01N 63/02* | (2006.01) |
| *C12N 1/20* | (2006.01) |
| *C12R 1/07* | (2006.01) |
| *A01N 31/08* | (2006.01) |
| *A01N 37/12* | (2006.01) |
| *C12R 1/085* | (2006.01) |
| *C12R 1/19* | (2006.01) |
| *C12R 1/385* | (2006.01) |
| *C12R 1/42* | (2006.01) |
| *C12R 1/445* | (2006.01) |
| *C12R 1/45* | (2006.01) |
| *C12R 1/46* | (2006.01) |

(52) U.S. Cl.
CPC ............. *A01N 63/02* (2013.01); *A01N 31/08* (2013.01); *A01N 37/12* (2013.01); *C12N 1/20* (2013.01); *C12R 1/07* (2013.01); *C12R 1/085* (2013.01); *C12R 1/19* (2013.01); *C12R 1/385* (2013.01); *C12R 1/42* (2013.01); *C12R 1/445* (2013.01); *C12R 1/45* (2013.01); *C12R 1/46* (2013.01)

(58) Field of Classification Search
None
See application file for complete search history.

(56) References Cited

U.S. PATENT DOCUMENTS 6,413,501 B2 * 7/2002 Tsuchiya ................. A61K 8/66
424/50

OTHER PUBLICATIONS

Riazi et al., Journal of Applied Microbiology, 2009, vol. 106, p. 1370-1377.*

* cited by examiner

*Primary Examiner* — Kade Ariani (57) ABSTRACT

Process of inhibiting microbial biofilm formation using extracellular metabolite composition from *Bacillus coagulans* MTCC 5856 and composition comprising from about 61% w/w of thymol, about 38% w/w of monolaurin and about 1% w/w of magnolol obtained from supercritical fluid extracts of *Magnolia officinalis* is described.

3 Claims, 14 Drawing Sheets

METHOD OF PRODUCING PARTIALLY PURIFIED EXTRACELLULAR METABOLITE PRODUCTS FROM *BACILLUS COAGULANS* AND BIOLOGICAL APPLICATIONS THEREOF

CROSS-REFERENCE TO RELATED PATENT APPLICATION

This patent application is a divisional application of U.S. patent application Ser. No. 14/576,411 filed on 19 Dec. 2014, which in turn is the non-provisional filing for provisional patent application 61/920,567 filed 24 Dec. 2013 for the invention titled "METHOD OF PRODUCING PARTIALLY PURIFIED EXTRACELLULAR METABOLITE PRODUCTS FROM *BACILLUS COAGULANS* AND BIOLOGICAL APPLICATIONS THEREOF," the subject matter of which is being incorporated herein in its entirety.

BACKGROUND OF THE INVENTION

Field of the Invention

The invention in general relates to the anti-microbial effects of probiotic preparations. More specifically, the present invention relates to (1) a method for producing partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050 and (2) the anti-microbial profile of said extracellular metabolite preparation against a panel of microbial pathogens, including synergistic anti-microbial effects of preparation when combined with a synergistic preservative blend comprising from about 61% w/w of thymol, about 38% of monolaurin and about 1% w/w of magnolol obtained from supercritical fluid extracts of *Magnolia officinalis*. The extracellular metabolite preparation alone or the combination of said extracellular metabolite preparation and preservative blend is also shown to inhibit microbial biofilm formation in a synergistic manner.

Description of Prior Art

Extracellular products of *Bacillus coagulans* comprising a supernatant or filtrate of a culture *Bacillus coagulans* strain suitable for topical application to the skin or mucosal membranes of a mammal and thereby capable of being utilized to inhibit the growth of bacterium, yeast; fungi; virus, and combinations thereof is known in the art (U.S. Pat. No. 6,905,692, "Topical compositions containing probiotic *Bacillus* bacteria, spores, and extracellular products and uses thereof). The present invention pertains to further purification of extracellular components of cultures of probiotic *Bacillus coagulans* SBC37-01 (Deposited in the Microbial Type Culture Collection and Gene Bank and was assigned the strain number MTCC 5856) to obtain a concentrated extracellular metabolite preparation that exhibits enhanced anti-microbial effects when compared to the supernatant itself both alone and when combined with a synergistic preservative blend comprising from about 61% w/w of thymol, about 38% of monolaurin and about 1% w/w of magnolol obtained from supercritical fluid extracts of *Magnolia officinalis*.

It is the principle objective of the present invention to disclose

1) A method for producing partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050.

2) The anti-microbial profile of said extracellular metabolite preparation against a panel of microbial pathogens, including synergistic anti-microbial effects of preparation when combined with a synergistic preservative blend comprising from about 61% w/w of thymol, about 38% of monolaurin and about 1% w/w of magnolol obtained from supercritical fluid extracts of *Magnolia officinalis*.

3) The microbial biofilm inhibitory potential of said extracellular metabolite preparation alone or in combination with a synergistic preservative blend comprising from about 61% w/w of thymol, about 38% of monolaurin and about 1% w/w of magmolol obtained from supercritical fluid extracts of *Magnolia officinalis*.

The present invention fulfills the aforesaid objectives and provides further related advantages.

DEPOSIT OF BIOLOGICAL MATERIAL

The deposit of biological material *Bacillus coagulans* SBC37-01 bearing accession number MTCC 5856, mentioned in the instant application has been made on 19 Sep. 2013 at Microbial Type Culture Collection & Gene Bank (MTCC), CSIR-Institute of Microbial Technology. Sector 39-A, Chandigarh—160036, India.

SUMMARY OF THE INVENTION

The present invention describes (1) A method for producing partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050;

(2) The antimicrobial profile of said extracellular metabolite preparation against a panel of microbial pathogens, including synergistic anti-microbial effects of preparation when combined with a synergistic preservative blend comprising from about 61% w/w of thymol, about 38% of monolaurin and about 1% w/w of magnolol obtained from supercritical fluid extracts of *Magnolia officinalis* and (3) The microbial biofilm inhibitory potential of said extracellular metabolite preparation alone or in combination with a synergistic preservative blend comprising from about 61% w/w of thymol, about 38% of monolaurin and about 1% w/w of magnolol obtained from supercritical fluid extracts of *Magnolia officinalis*.

(4) The antimicrobial activity and anti-acidogenic effect against adherent *S. mutans* in water-insoluble glucans of said extracellular metabolite preparation alone at in combination with a synergistic preservative blend comprising from about 61% w/w of thymol, about 38% of monolaurin and about 1% w/w of magnolol obtained from supercritical fluid extracts of *Magnolia officinalis*.

The present invention provides the following advantages.
1) Disclosure of a purification method for producing partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050;
2) Disclosure of the anti-microbial profile of the partially purified against a panel of microbial pathogens, including synergistic anti-microbial effects of said partially purified extracellular preparation when combined with a synergistic preservative blend comprising from about 61% w/w of thymol, about 38% of monolaurin and about 1% w/w of magnolol obtained from supercritical fluid extracts of *Magnolia officinalis*.
3) Disclosure of the microbial biofilm inhibitory potential of said extracellular metabolic preparation alone or in combination with a synergistic preservative blend comprising from about 61% w/w of thymol, about 38% of monolaurin and about 1% w/w of magnolol obtained from supercritical fluid extracts of *Magnolia officinalis*.
4) Disclosure of the antimicrobial activity and anti-acidogenic effect against adherent *S. mutans* in water-insoluble glucans, of said extracellular metabolite preparation alone or in combination with a synergistic preservative blend comprising from about 61% w/w of thymol, about 38% of monolaurin and about 1% w/w of magnolol obtained from supercritical fluid extracts of *Magnolia officinalis*.

Other features and advantages of the present invention will become apparent from the following more detailed description, taken in conjunction with the accompanying images, which illustrate, by way of example, the principle of the invention.

DETAILED DESCRIPTION OF THE MOST PREFERRED EMBODIMENT

In the most preferred embodiment the present invention relates to a purification method for producing partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050, said purification method comprising the steps of:
1. Inoculating a culture of *Bacillus coagulans* MTCC 5856 exhibiting 99% genetic homology with the known bacterial strains *Bacillus coagulans* ATCC 31284, *Bacillus coagulans* NBRC 3887 and *Bacillus coagulans* ATCC 7050 into 1.0 liter of Glucose Yeast Extract Acetate broth medium (HiMedia, Mumbai India) or MRS broth containing 0.5% tween 80 or Corn steep powder media;
2. Allowing the fermentation in the inoculated medium of step 1 to proceed for 24-48 h at 37° C. with 120 rpm;
3. Centrifuging the fermentation broth of step 2 at 4000-7000 rpm:
4. Concentrating supernatants 10 fold by using rotary evaporator at 50° C. of step 3.
5. Adding 150 ml of chilled acetone drop by drop to 100 ml of tenfold concentrated supernatants of step 4, followed by mixing;
6. Incubating the mixture of step 5 at 0° C. fix 30 minutes followed by centrifuging at 7000-8000 rpm;
7. Discarding the pellet obtained in step 6 and collecting 60% acetone saturated supernatant (~200 ml).
8. Concentrating the acetone saturated supernatant in step 7 to 50 ml by rotary evaporator.
9. Adjusting the pH to 5.0 by using, 4N HCl, filtered (0.22 micron; Millex, Millipore, India) and stored at −20° C. till further use.
10. Freeze drying/spray drying/tray drying the supernatant of step 8.

In another most preferred embodiment, the present invention relates to a process of microbial control, said process comprising the step of bringing into contact effective concentrations of a partially purified extracellular metabolite preparation from probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050 and a target microbial cell. In more specific embodiments, the microbial cell may be one selected from the group comprising *Pseudomonas aeruginosa*, *Escherichia coli*, *Staphylococcus aureus*, *Staphylococcus epider-* midis, *Streptococcus mutans, Propionibacterium acnes, Bacillus cereus* and *Salmonella abony*.

In yet another most preferred embodiment, the present invention relates to a process of microbial control, said process comprising the step of bringing into contact a microbial cell with effective concentrations of a preparation consisting essentially of partially purified extracellular metabolite preparation from probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050 and a synergistic preservative blend comprising from about 61% w/w of thymol, about 38% of monolaurin and about 1% w/w of magnolol obtained from supercritical fluid extracts of *Magnolia officinalis*. In more specific embodiments, the microbial cell may be one selected from the group comprising *Pseudomonas aeruginosa, Escherichia coli, Staphylococcus aureus, Staphylococcus epidermidis, Streptococcus mutans, Propionibacterium acnes, Bacillus cereus* and *Salmonella abony*.

In yet another most preferred embodiment, the present invention also relates to a process of inhibiting microbial biofilm formation, said process comprising step of bringing into contact biofilm producing microbial cells and a preparation consisting essentially of partially purified extracellular metabolite preparation from probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887 and *Bacillus coagulans* ATCC 7050 alone or said preparation combined with a synergistic preservative blend comprising from about 61% w/w of thymol, about 38% of monolaurin and about 1% w/w of magnolol obtained from supercritical fluid extracts of *Magnolia officinalis*.

The following examples are presented herewith to illustrate the exemplary embodiments of the present invention.

EXAMPLE 1

Microorganisms and Culture Conditions

The bacterial strains used in this study included *Streptococcus mutans* MTCC 1943, *Staphylococcus aureus* ATCC 29213, *Staphylococcus epidermidis* ATCC 14990, *Escherichia coli* ATCC 25922, *Pseudomonas aeruginosa* ATCC 9027, *Salmonella abony* NCIM 2257 and *Bacillus cereus* ATCC 14579. The reference strains were purchased from ATCC (American Type Culture Collection, Manassas, Va., USA), MTCC (IMTECH, Chandigarh, India) and NCIM (National Collection of Industrial Microorganisms, Pune, India). *S. mutans* and *P. acnes* were maintained on brain-heart infusion agar (BHI; Difco Laboratories, Detroit, Mich., USA) and reinforced clostridial agar (RCA; HiMedia, Mumbai, India) respectively. *S. aureus, S. epidermidis E. coli, P. aeruginosa, S. abony* and *B. cereus* were maintained on trypticase soy agar (Difco Laboratories) at 37° C. *S. mutans* and *P. acnes* were incubated anaerobically (80% $N_2$, 10% $H_2$ and 10% $CO_2$) at 37° C. up to 48 h in anaerobic chamber (Coy Laboratory Products Inc, Michigan). *Bacillus coagulans* SBC37-01 used in the study was characterized and deposited to Microbial Type Culture Collection, Chandigarh, India and the strain was assigned as *Bacillus coagulans* MTCC 5856.

Technique—The Checkerboard Method for Synergy Study

Figure 1:
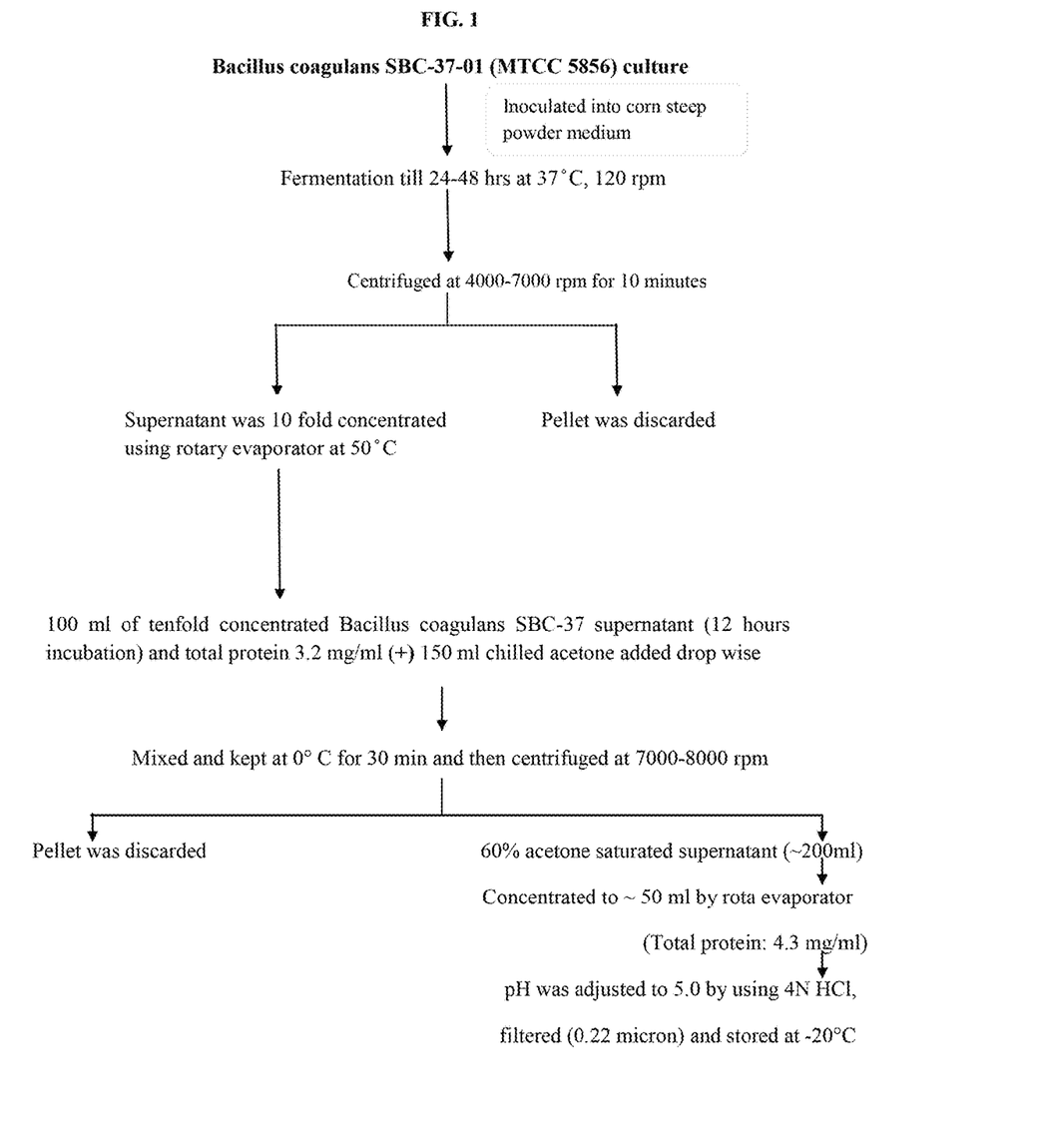
FIG. 1 shows the process flowchart for a purification method to produce partially purified extracellular metabolite preparation from the probiotic bacterial strain *Bacillus coagulans* SBC37-01 (Deposited in the Microbial Type Culture Collection and Gene Bank and was assigned the strain number MTCC 5856) exhibiting 99% genetic homology with the known bacterial strains *Bacillus coagulans* ATCC 31284, *Bacillus coagulans* NBRC 3887and *Bacillus coagulans* ATCC 7050.
Figure 2:
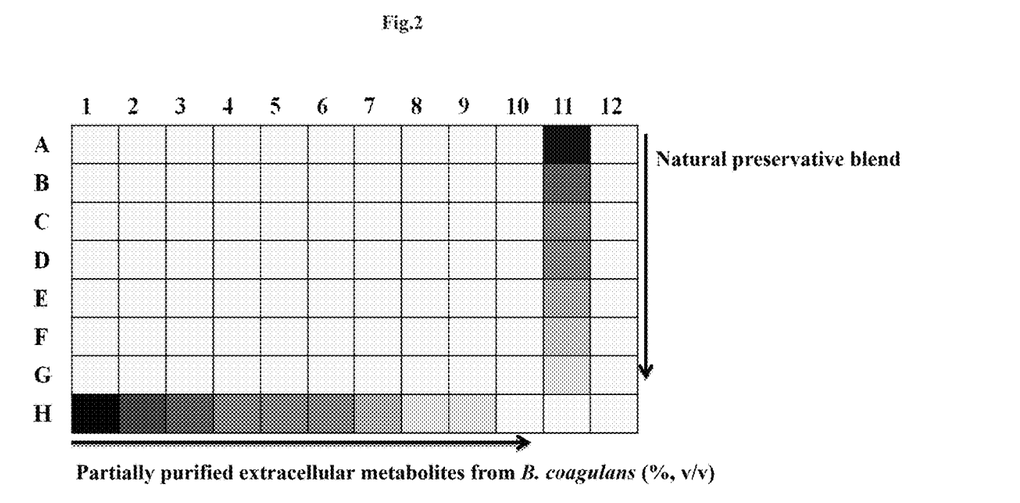
FIG. 2 shows the representation of checkerboard broth micro-dilution method for synergistic anti-microbial studies.
Figure 3A:
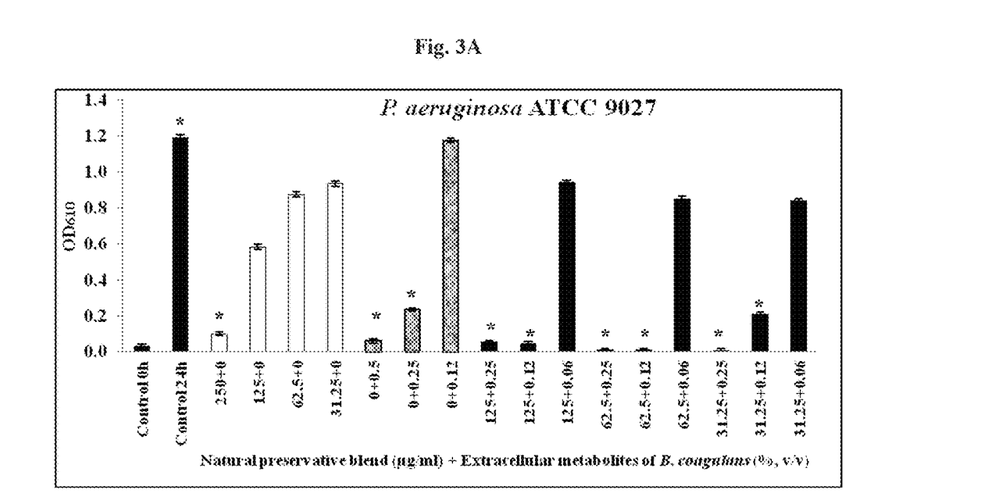
FIGS. 3A-3B, 3C-3D, 3E-3F, 3G-3H, 3I-3J, 3K-3L, 3M-3N, 3O-3P show respectively, the graphical representation of the effect of natural preservative blend and extracellular metaboliltes of *B. coagulans* MTCC 5856 alone and in combination on the growth and viability of *Pseudomonas aeruginosa* ATCC 9027, *Escherichia coil* ATCC 25922, *Salmonella abony* NCIM 2257, *Streptococcus mutans* MTCC 1943, *Propionibacterium acnes* ATCC 11827, *Staphylococcus aureus* ATCC 29213, *Staphlococcus epidermidis* ATCC 14990 and *Bacillus cereus* ATCC 14579.
Figure 3B:
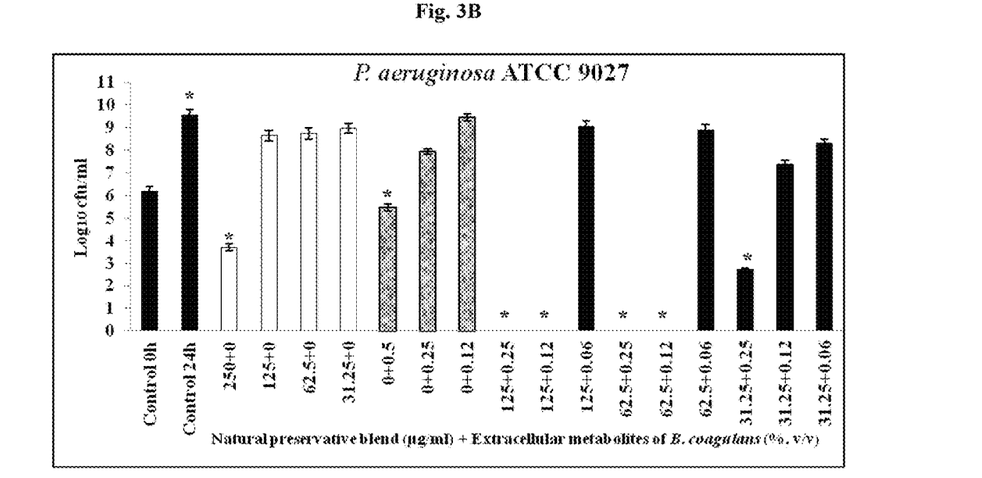
Figure 3C:
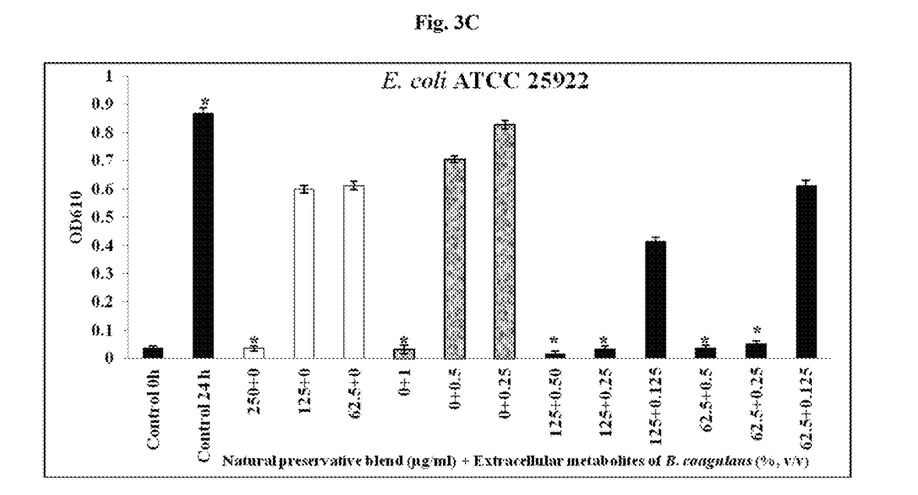
Figure 3D:
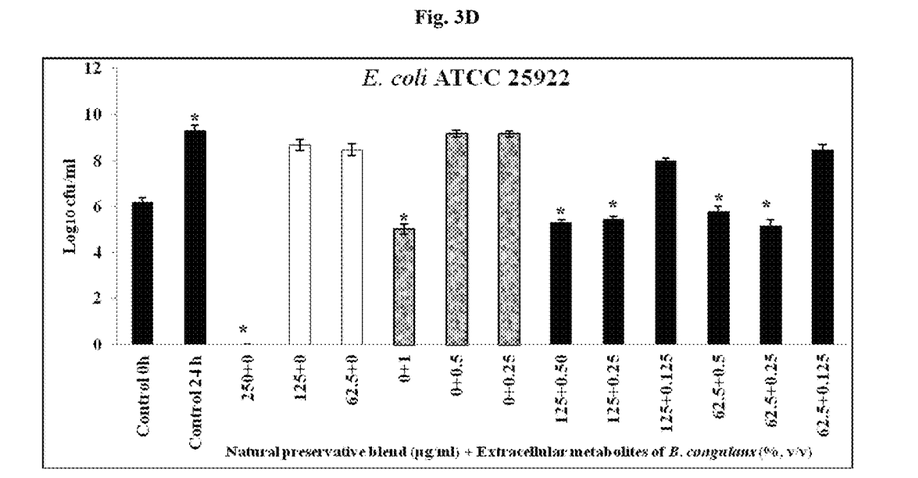
Figure 3E:
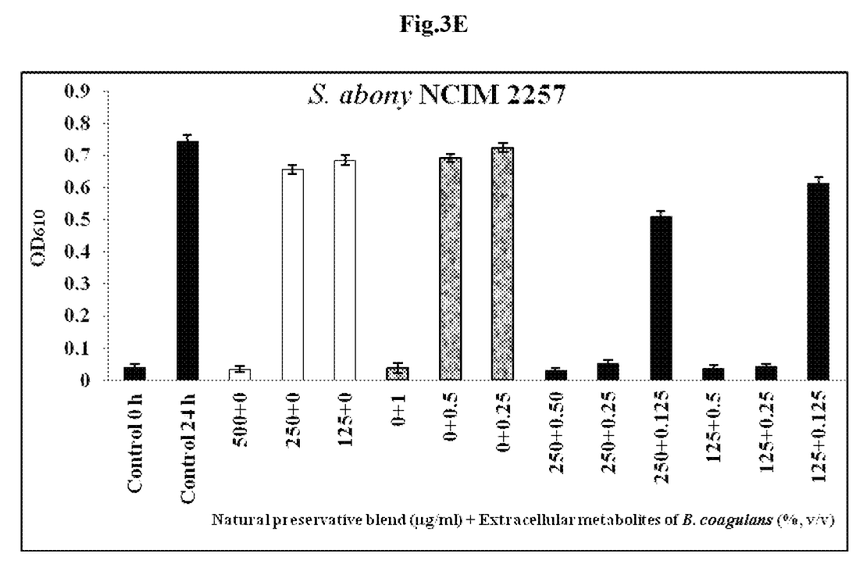
Figure 3F:
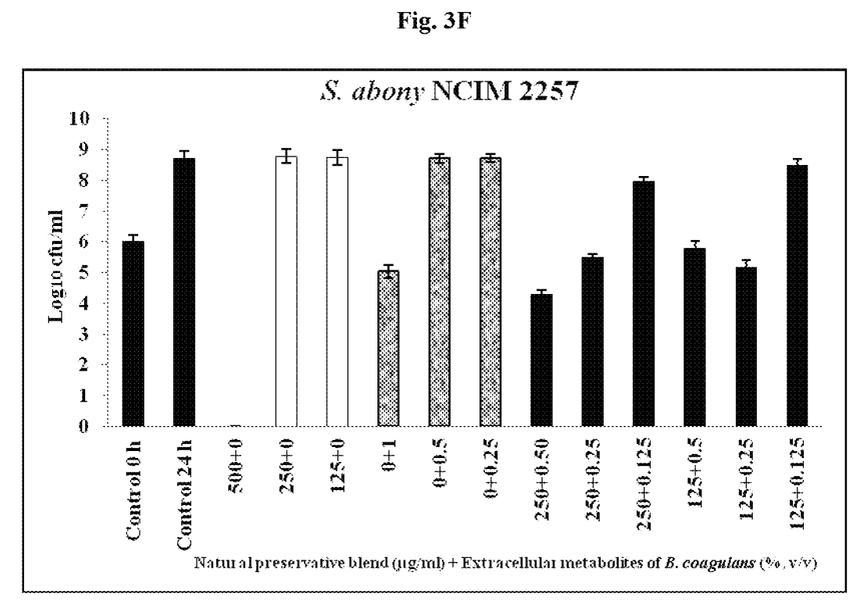
Figure 3G:
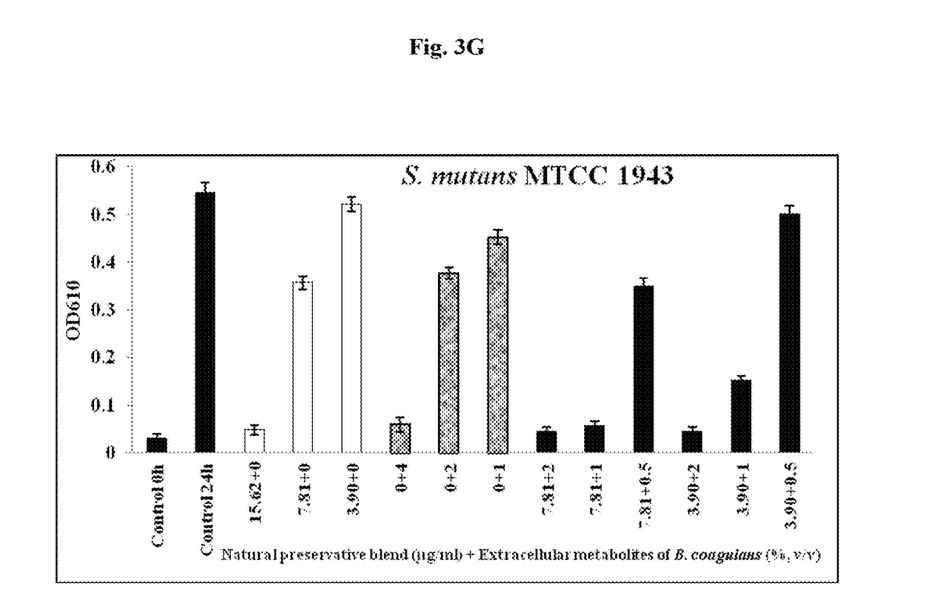
Figure 3H:
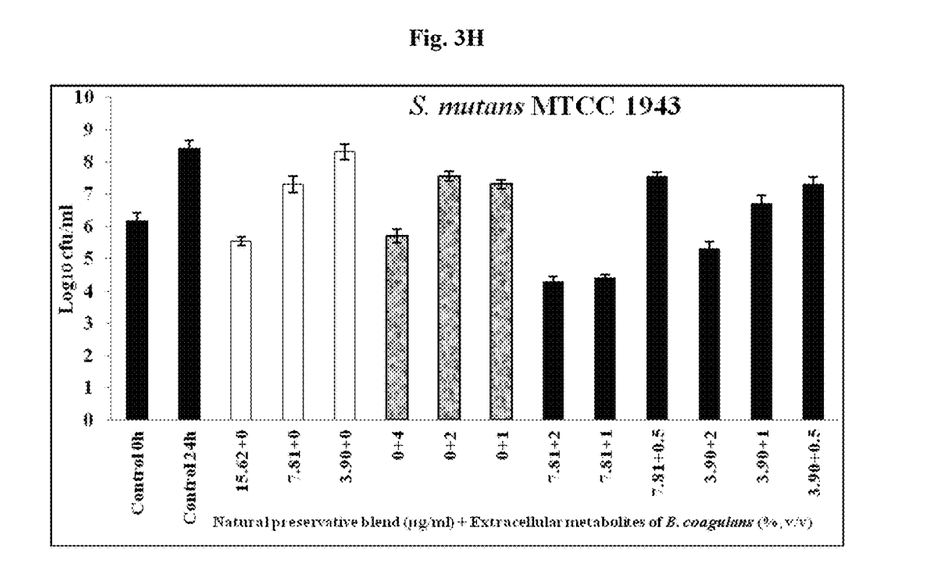
Figure 3I:
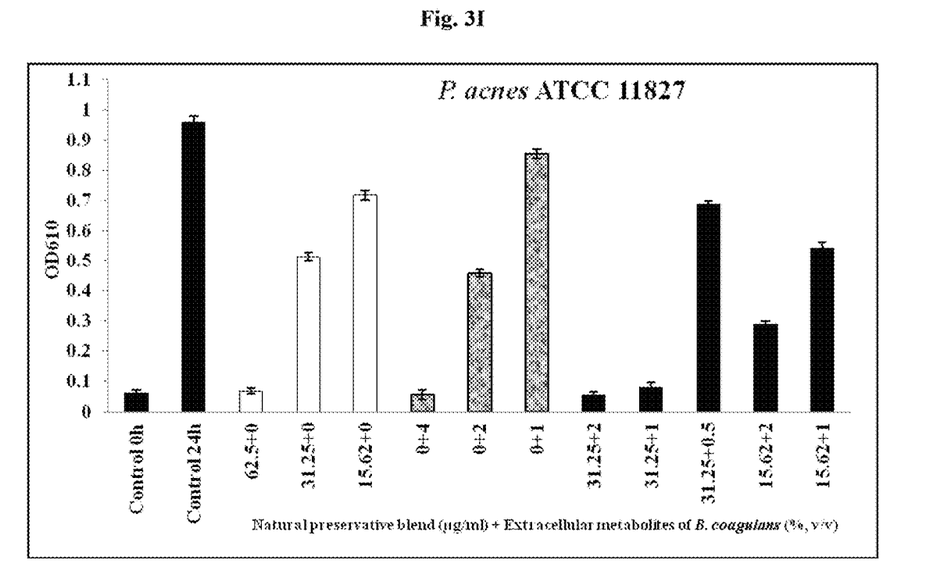
Figure 3J:
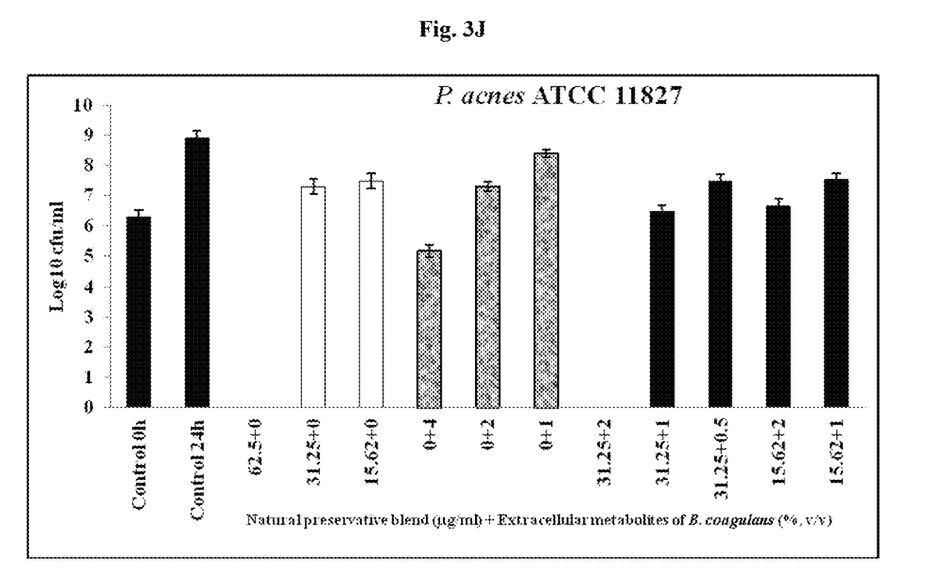
Figure 3K:
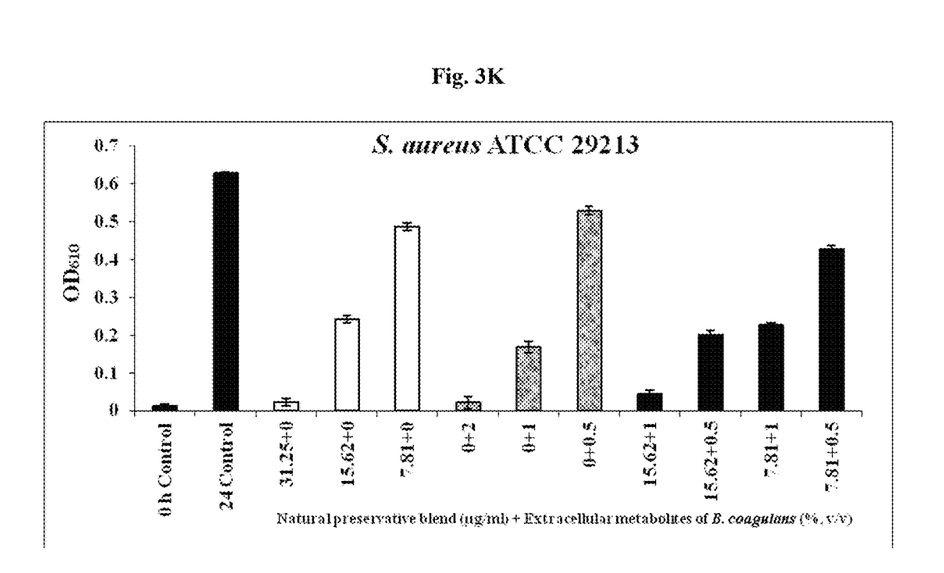
Figure 3L:
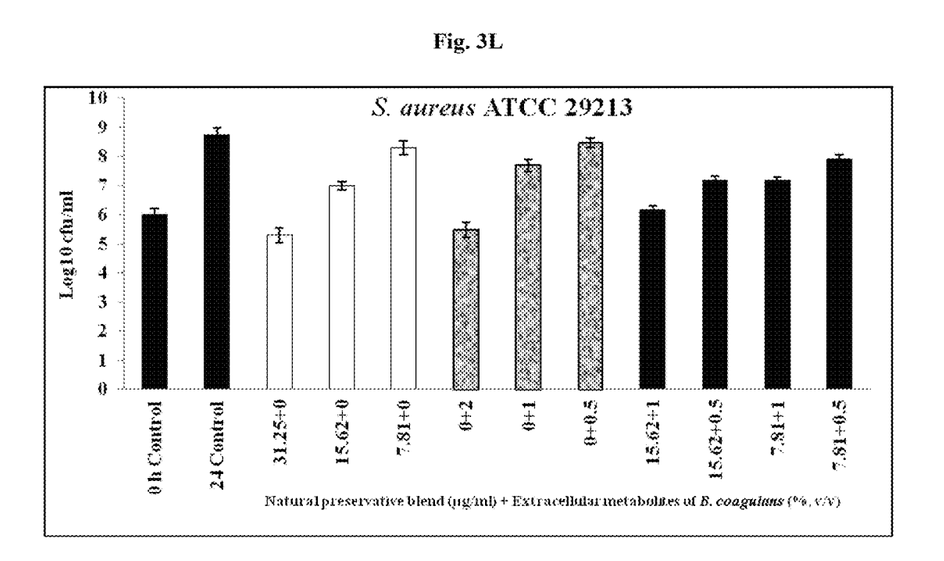
Figure 3M:
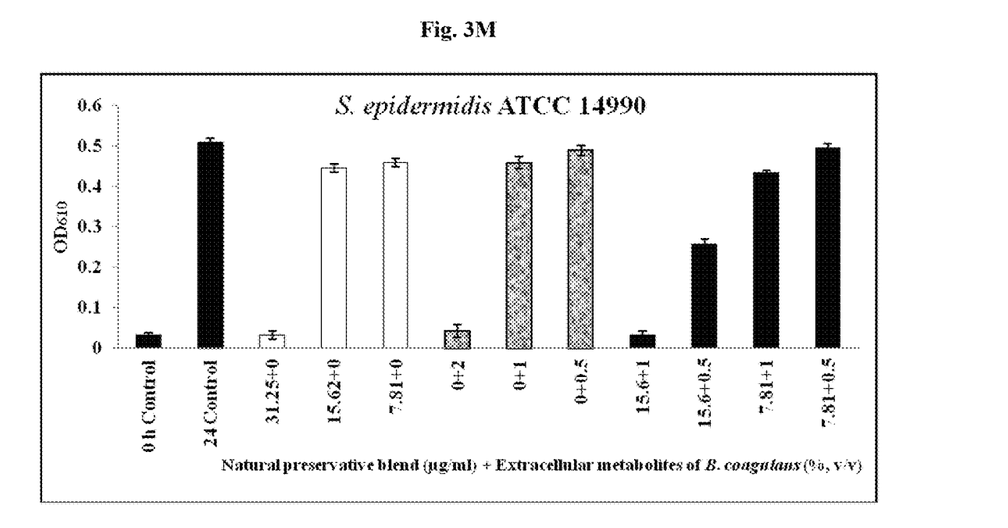
Figure 3N:
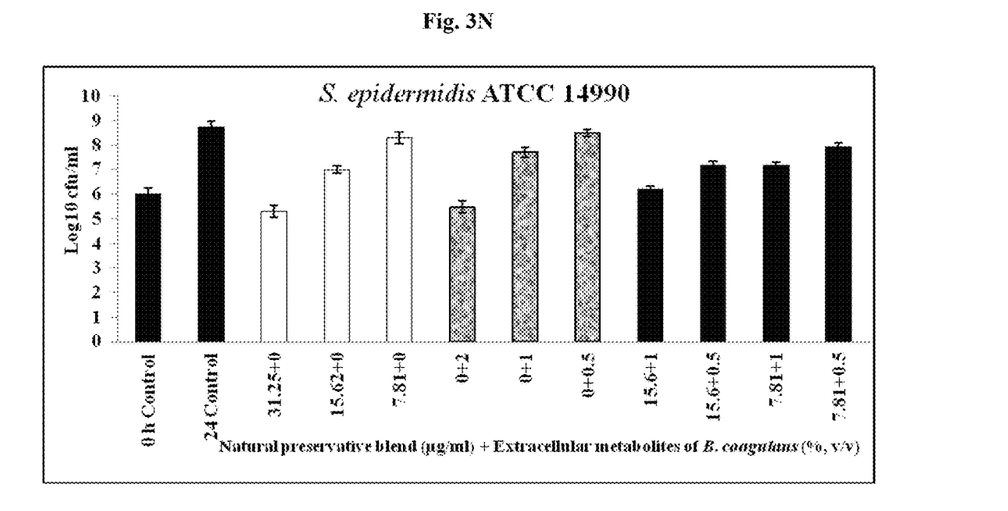
Figure 3O:
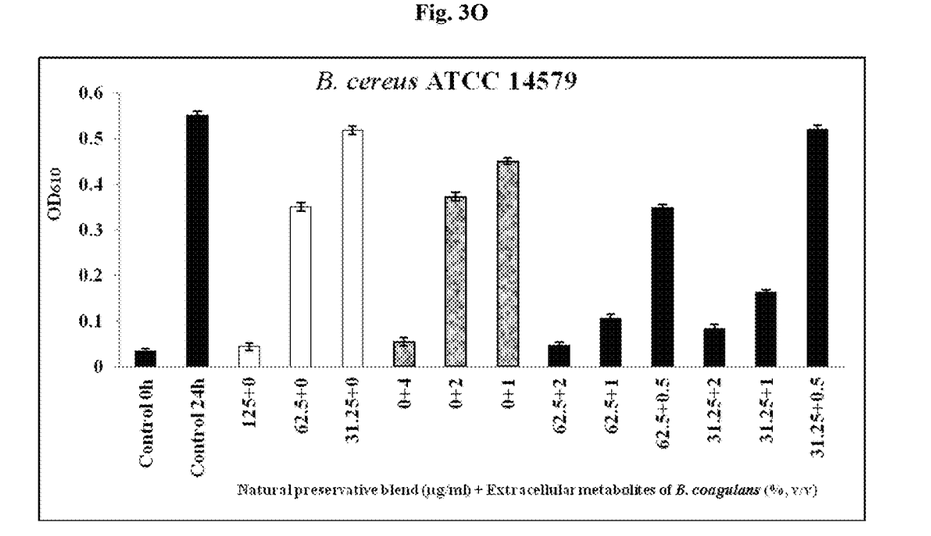
Figure 3P:
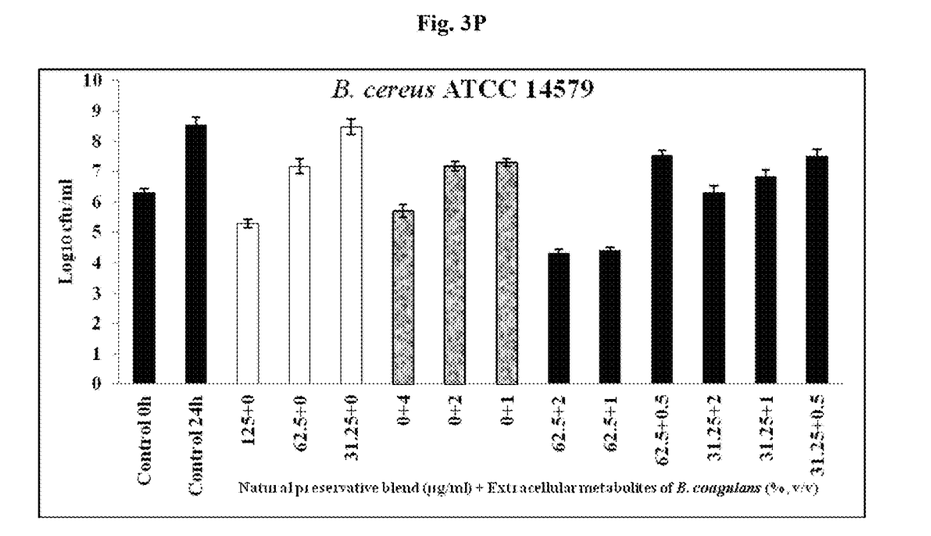
Figure 4A:
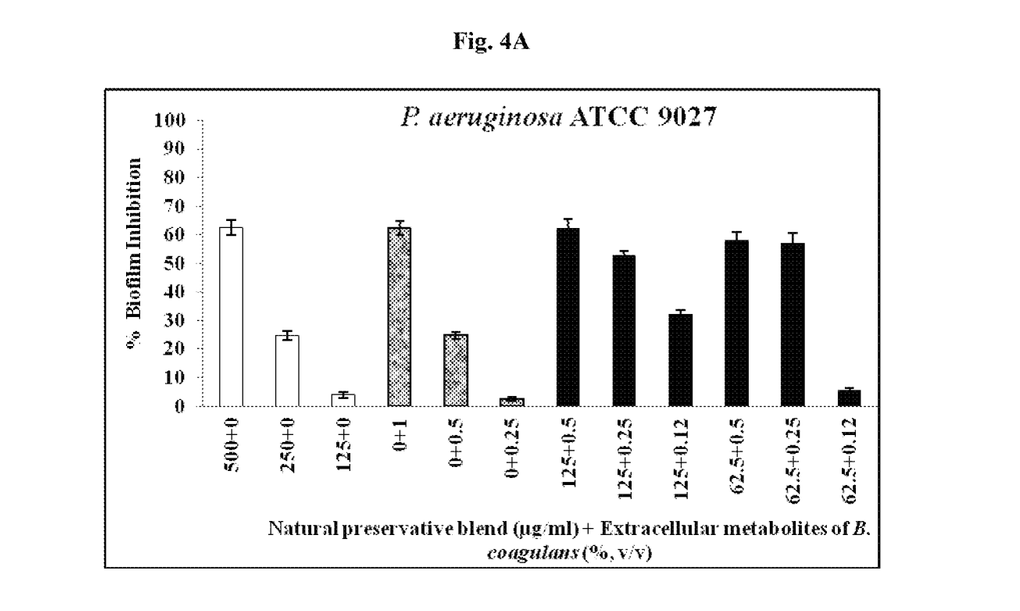
FIGS. 4A. 4B, 4C, 4O and 4E show respectively, the graphical representations of the effect of natural preservative blend and extracellular metabolites of *B. coagulans* MTCC 5856 alone and in combination on the biofilm formation of *Pseudomonas aeruginosa* ATCC 9027, *Escherichia coli* ATCC 25922, *Streptococcus mutans* MTCC 1943, *Staphylococcus aureus* ATCC 29213 and *Staphylococcus epidermidis* ATCC 14990.
Figure 4B:
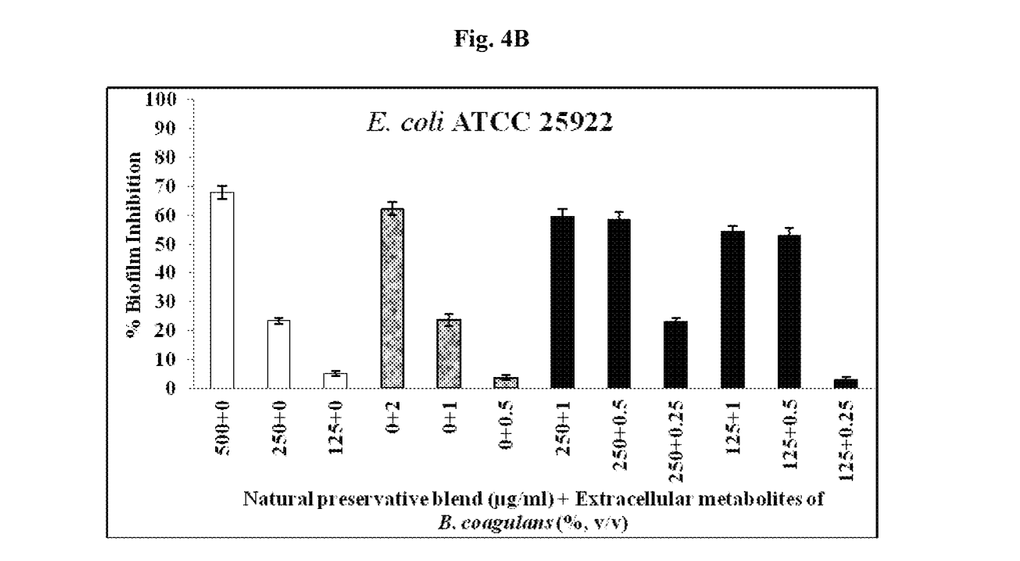
Figure 4C:
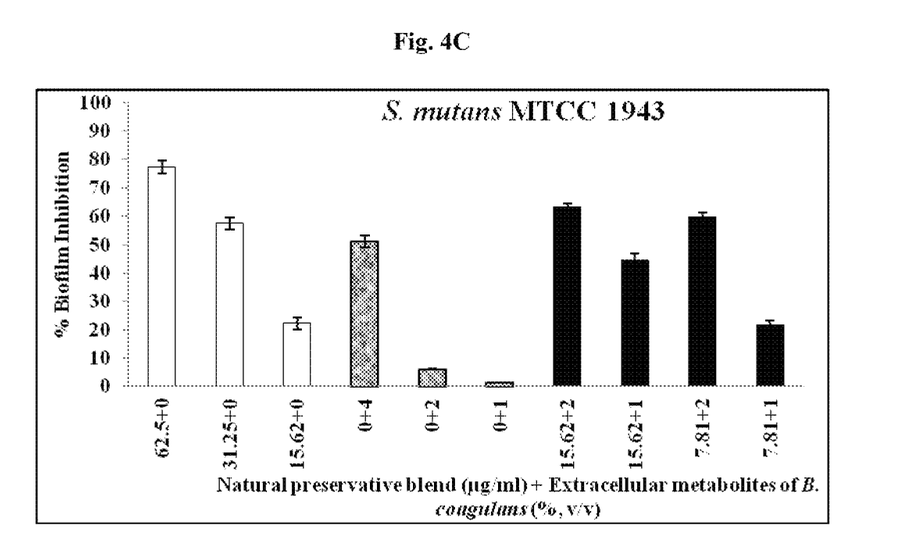
Figure 4D:
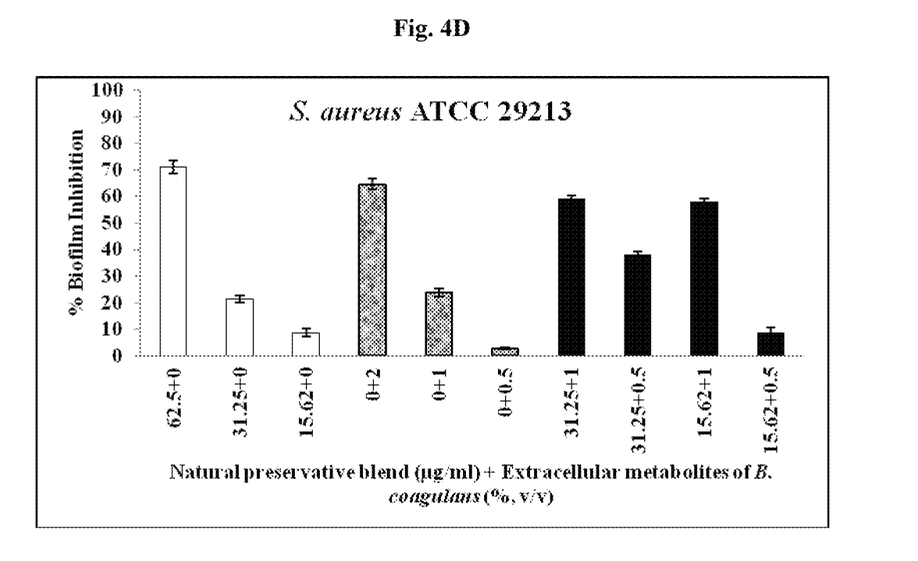
Figure 4E:
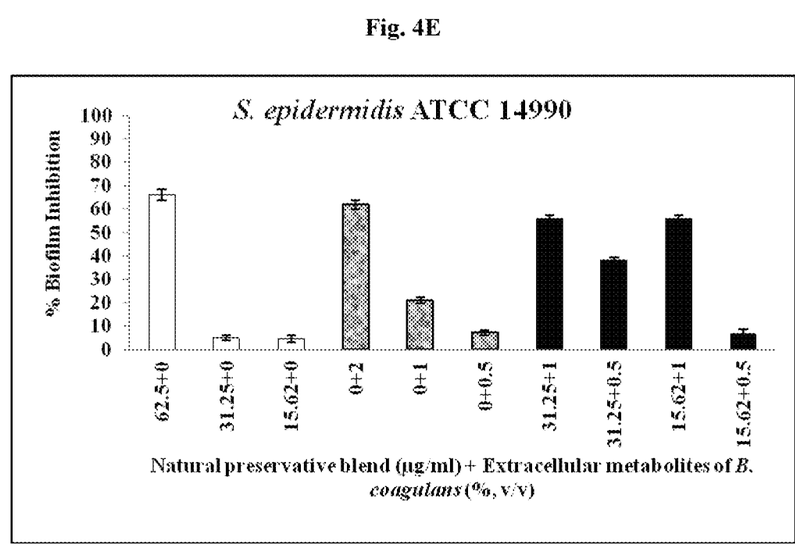
Figure 5A:
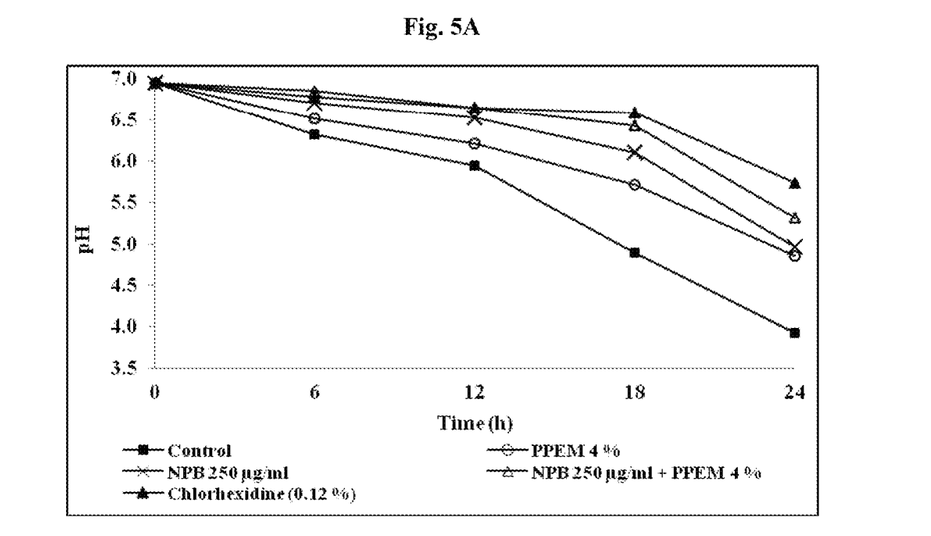
FIGS. 5A and 5B show respectively, the graphical representations of the effect of natural preservative blend and extracellular metabolites of *B. coagulans* MTCC 5856 on the growth/pH drop and the formation of water insoluble glucans of *S. mutans* MTCC 1943 biofilm in presence of 2% sucrose.
Figure 5B:
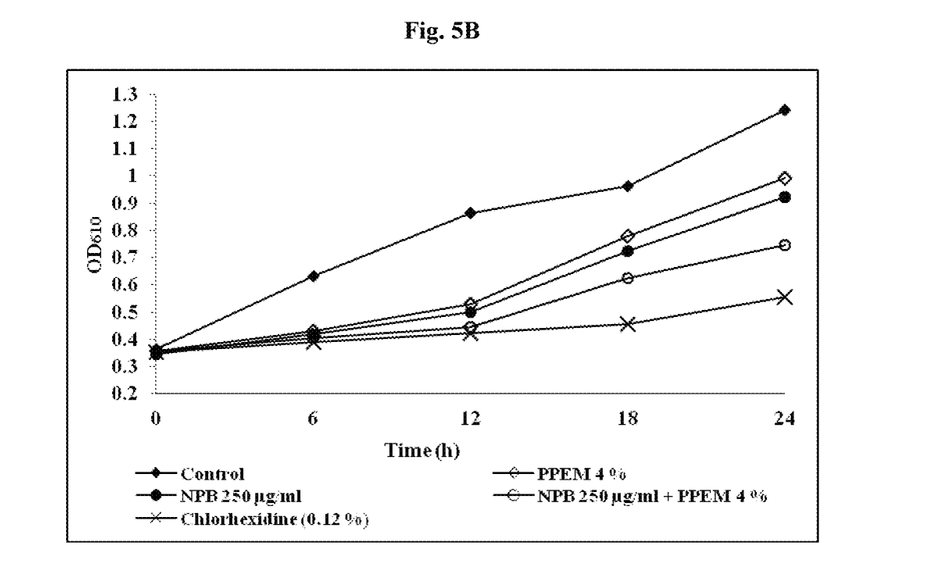

This is the most frequently used method to access the antimicrobial combinations in vitro. The term, "checkerboard" refers to the pattern (of tubes or microtiter plate wells) formal by multiple dilutions of two drugs being tested (Eliopoulos G M, Moellering R C: Antimicrobial combinations. In Antibiotics in laboratory medicine. Edited by Lorian V. Baltimore, The Williams & Wilkins Co; 1991: 432-492). In the present study, the checker board consisted of columns in which each tube (or well) contains the same amount of the partially purified extracellular metabolite preparation from the probiotic bacterial strain *Bacillus coagulans* MTCC 5856 being diluted along the X-axis (rows) in which each tube (or well) contains the same amount of the preservative blend being diluted on the Y-axis (FIG. 2). As a result each square in the checkerboard (which represents one tube/well or plate) contained a unique combination of partially purified extracellular metabolite preparation from the probiotic bacterial strain *Bacillus coagulans* MTCC 5856 and preservative blend. The concentration range of preservative blend in the present study was 2000 µg/ml to 31.25 µg/ml and lower in some cases, whereas the partially purified extracellular metabolite preparations from the probiotic bacterial strain *Bacillus coagulans* MTCC 5856 was tested in the range of 8% (v/v) to 0.015% (v/v). This checkerboard technique can be performed with liquid or semisolid (agar) media. BHI broth and RC broth were used for *S. mutans* and *P. acnes* respectively and plates were incubated anaerobically (80% $N_2$, 10% $H_2$ and 10% $CO_2$) at 37° C. up to 48 h in anaerobic chamber. Mueller hinton broth (Difco) was used for *S. aureus, S. epidermidis E. coli, P. aeruginosa, S. abony* and *B. cereus* and plates were incubated at 37° C. for 18 h.

Kill Kinetics

Time-kill studies of the preservative blend and partially purified extracellular metabolite preparation from strain *Bacillus coagulans* MTCC 5856 were conducted against *P. aeruginosa, E. coli, S. aureus S. epidermidis, S. mutans, P. acnes, B. cereus* and *Salmonella abony* and evaluated using a time-kill curve method, as described previously (Eliopoulus G M, Moellering R C J. Antimicrobial combinations. In: Lorin V, ed. Antibiotics in Laboratory Medicine, 4th edn. Baltimore: Williams & Wilkins, 1996; 330-6.). Bacterial suspension in its logarithmic phase ($1 \times 10^6$ cfu/ml) was used as the inoculum. The preservative blend and partially purified extracellular metabolite preparation from strain *Bacillus coagulans* MTCC 5856 were tested alone and in combination at different concentrations, as determined in checkerboard assay. The cell population as cfu/ml was determined by a serial dilution method in triplicate on respective media and incubated in respective growth conditions. The viable count and absorbance ($OD_{610}$) were taken at 0 (untreated control), and 24 h of incubation at 37° C. Viable count was expressed in $Log_{10}$ cfu/ml and absorbance was expressed in OD value at 610 nm.

Biofilm Susceptibility Assays

The biofilm inhibitory effect of preservative blend and partially purified extracellular metabolite preparation from the strain *Bacillus coagulans* MTCC 5856 alone and in combination were examined against *S. mutans, E. coli, S. aureus S. epidermidis* and *P. aerugenosa* by the microdilution method (Wei et al. Journal of Antimicrob. Chemother, 2006, 57:1100-1109.). This method was similar to the checkerboard method for planktonic cells. For *S. mutans* biofilm assay, BHI broth supplemented with 2% sucrose was used. In case of other organisms, TSB supplemented with 2% glucose was used in the study. The bacterial suspensions were prepared from the overnight-grown culture, and the turbidity of the suspension was adjusted to an optical density at 610 nm ($A_{610}$) of 0.7 ($1 \times 10^9$ CFU/ml). The concentration range of preservative blend in the present study was 2000 µg/ml to 31.25 µg/ml and lower concentrations in some cases, whereas partially purified extracellular metabolite preparation from the strain *Bacillus coagulans* MTCC 5856 was tested in the range of 8% (v/v) to 0.015% (v/v). Forty microliters of fresh media broth was added to each well, followed by the addition of 60 µl of the above-mentioned suspension to each well of the plate. This resulted in the final inoculum of $6 \times 10^7$ CFU/ml in each well; After incubation at 37° C. for 48 h, the culture supernatant from each well was decanted, and planktonic cells were removed by washing the wells with phosphate-buffered saline (PBS; pH 7.2). The biofilm was fixed with methanol for 15 min and then air dried at room temperature. The wells of the dried plate were stained with 0.1% (w/v) crystal violet (Sigma Chemical Co., St Louis, Mo.) for 10 min and rinsed thoroughly with water until the negative control wells appeared colorless. Biofilm formation was quantified by the addition of 200 µl of 95% ethanol to the crystal violet-stained wells and recording the absorbance at 595 nm ($A_{595}$). The percentage of biofilm inhibition was calculated using the equation ($A_{595}$ of biofilm treated with test agent/$A_{595}$ of non-treated control)×100. Culture without test agent was used as the non-treated control.

Antimicrobial Activity Against Adherent *S. Mutans* in Water-Insoluble Glucan The formation of water-insoluble glucan by *S. mutans* MTCC 1943 was performed by a previously described method (Katsura et al, Antimicrob. Agents Chemother, 2001, 45:3009-3013). Briefly, aliquots of 100 µl of culture of *S. mutans* MTCC 1943 (~$1 \times 10^8$ cells/ml) were inoculated into 10 ml of fresh BHI broth containing 2% sucrose (w/v) in the test tubes and incubated at 37° C. for 24 h at an inclination of 30°. The fluid containing planktonic cells was gently removed. The water-insoluble glucan containing cells of *S. mutans* MTCC 1943 were gently washed with 10 ml of sterile water and resuspended in 10 ml of phosphate buffer (10 mM, pH 5.0) containing preservative blend and partially purified extracellular metabolite preparation from the strain *Bacillus coagulans* MTCC 5856 alone and in combination, followed by incubation at 37° C. for 5 min. Chlorhexidine 0.12% (v/v) (Sigma Chemical Co., St Louis, Mo.) was used as internal reference in the study. The mixture was gently washed again with sterile saline (0.89% NaCl, w/v), followed by the resuspension of treated cells in 10 ml of BHI broth containing 2% sucrose (w/v). After incubation of cells at 37° C. for 6, 12, 18, and 24 h, the acid produced by the culture was measured by using a pH meter. The fluid containing free cells of *S. mutans* MTCC was gently removed. The water insoluble glucan was resuspended in 10 ml of 1 N NaOH solution and homogenized; the turbidity was measured at 610 nm.

RESULTS

Table 1 shows the fold reduction of human microbial pathogens when brought in contact with A. formulations containing just Partially Purified Extracellular Metabolites (PPEM) or Natural Preservative Blend (NPB); and B. formulations incorporating both Partially Purified Extracellular Metabolites (PPEM) and Natural Preservative Blend (NPB). It may be noted that the formulations incorporating both Partially Purified Extracellular Metabolites (PPEM) and Natural Preservative Blend (NPB) cause a significant eight fold decrease for pathogen *Pseudomonas aeruginosa* and four fold decrease for pathogen *Escherichia coli*.

TABLE 1

Results of checkerboard testing of the natural preservative blend and partially purified extracellular metabolites of probiotic stain *Bacillus coagulans* MTCC 5856 against human pathogens

| S. No | Tested organisms | Partially Purified Extracellular Metabolites (PPEM) MIC (%, v/v) | | Natural Preservative Blend (NPB) MIC (µg/ml) | |
|---|---|---|---|---|---|
| | | alone | In combination with NPB (Fold reduction in MIC) | alone | In combination with PPEM (Fold reduction in MIC) |
| 1 | *P. aeruginosa* ATCC 9027 | 0.5 | 0.12 (4) | 250 | 31.25 (8) |
| 2 | *E. coli* ATCC 25922 | 1.0 | 0.25 (4) | 250 | 62.50 (4) |
| 3 | *S. abony* NCIM 2257 | 1.0 | 0.25 (4) | 500 | 125 (4) |
| 4 | *S. mutans* MTCC 1943 | 4.0 | 2.0 (2) | 15.62 | 7.81 (2) |
| 5 | *P. acnes* ATCC 11827 | 4.0 | 2.0 (2) | 62.50 | 31.25 (2) |
| 5 | *S. aureus* ATCC 29213 | 2.0 | 1.0 (2) | 31.25 | 15.62 (2) |
| 6 | *S. epidermidis* ATCC 14990 | 2.0 | 1.0 (2) | 32.25 | 15.62 (2) |
| 7 | *B. cereus* ATCC 14579 | 4.0 | 2.0 (2) | 125 | 31.25 (2) |

While the invention has been described with reference to a preferred embodiment, it is to be clearly understood by those skilled in the art that the invention is not limited thereto. Rather, the scope of the invention is to be interpreted only in conjunction with the appended claims.

We claim:

1. A process of inhibiting microbial biofilm formation, said process comprising a step of bringing into contact biofilm producing microbial cells and a preparation consisting of partially purified extracellular metabolites of probiotic bacterial strain *Bacillus coagulans* deposited under accession number MTCC 5856, prepared by partially purifying a culture supernatant of said *Bacillus coagulans* strain, alone or combined with a composition comprising from about 61% w/w of thymol, about 38% w/w of monolaurin, and about 1% w/w of magnolol obtained from supercritical fluid extracts of *Magnolia officinalis*, thereby inhibiting said biofilm formation.

2. A process of preventing pH drop and further accumulation of biofilm of *Streptococcus mutans* in presence of sucrose, said process comprising a step of bringing into contact biofilm/plaque producing *Streptococcus mutans* and a preparation consisting essentially of partially purified extracellular metabolites of probiotic bacterial strain *Bacillus coagulans* deposited under accession number MTCC 5856, prepared by partially purifying a culture supernatant of said *Bacillus coagulans* strain, alone or combined with a composition comprising from about 61% w/w of thymol, about 38% w/w of monolaurin, and about 1% w/w of magnolol obtained from supercritical fluid extracts of *Magnolia officinalis*, thereby preventing pH drop and biofilm accumulation.

3. A process of preventing pH drop and further accumulation of biofilm of *Streptococcus mutans* in presence of sucrose, said process comprising step of bringing into contact biofilm/plaque producing *Streptococcus mutans* and a preparation consisting essentially of partially purified extracellular metabolite preparation from probiotic bacterial strain *Bacillus coagulans* MTCC 5856 alone or said preparation combined with a composition comprising from about 61% w/w of thymol, about 38% w/w of monolaurin and about 1% w/w of magnolol obtained from supercritical fluid extracts of *Magnolia officinalis*, to prevent such drop in pH and biofilm accumulation.

* * * * *